United States Patent [19]

Hoeffkes et al.

[11] Patent Number: 4,820,511
[45] Date of Patent: Apr. 11, 1989

[54] HAIR CARE AND AFTERTREATMENT PREPARATIONS

[75] Inventors: Horst Hoeffkes, Duesseldorf; Fritz Lange, Essen; Karl Giede, Hilden, all of Fed. Rep. of Germany

[73] Assignee: Henkel Kommanditgesellschaft auf Aktien, Duesseldorf, Fed. Rep. of Germany

[21] Appl. No.: 89,714

[22] Filed: Aug. 26, 1987

[30] Foreign Application Priority Data

Aug. 29, 1986 [DE] Fed. Rep. of Germany ....... 3629510

[51] Int. Cl.$^4$ .......................... A61K 7/06; A61K 7/08; A61K 7/11
[52] U.S. Cl. ........................................ 424/70; 424/71; 252/547; 564/294
[58] Field of Search .................. 424/70, 71, DIG. 2; 252/547, DIG. 13, 174.21; 564/294

[56] References Cited

U.S. PATENT DOCUMENTS

| | | | |
|---|---|---|---|
| 2,798,053 | 7/1957 | Brown | 260/2.2 |
| 3,472,840 | 10/1969 | Stone | 260/231 |
| 3,632,559 | 1/1972 | Matter | 260/78 SC |
| 3,910,862 | 10/1975 | Barabas | 260/79.3 MU |
| 3,912,808 | 10/1975 | Sokol | 424/71 |
| 4,134,970 | 1/1979 | Panke et al. | 424/70 |
| 4,157,388 | 6/1979 | Christiansen | 424/70 |
| 4,650,865 | 3/1987 | Lange et al. | 564/347 X |

FOREIGN PATENT DOCUMENTS

| | | |
|---|---|---|
| 0190708 | 2/1986 | European Pat. Off. . |
| 2628157 | 5/1978 | Fed. Rep. of Germany . |
| 3629510 | 3/1988 | Fed. Rep. of Germany . |

*Primary Examiner*—Ellis P. Robinson
*Assistant Examiner*—Susan S. Rucker
*Attorney, Agent, or Firm*—Ernest G. Szoke; Wayne C. Jaeschke; Henry E. Millson, Jr.

[57] ABSTRACT

Cosmetic compositions for hair care and aftertreatment include a surface-active quaternary ammonium compound of the following formula:

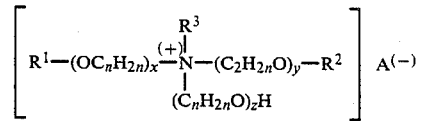

wherein $R^1$ and $R^2$ are $C_8$–$C_{22}$-alkyl; $R^3$ is $C_1$–$C_4$-alkyl, benzyl, or —$(C_nH_{2n}O)z$; n is 2 or 3; x, y, and z are 1–20; and A is an anion; as hair revitalizing agents with particularly good emulsifying properties. In one embodiment, the compositions are in the form of oil-in-water emulsions useful as hair rinses and contain from 0.1 to 5% by weight of the quaternary ammonium compound and from 0.2 to 10% by weight of a water-insoluble oil or fatty component, especially a $C_{12}$–$C_{18}$ fatty alcohol, a mono- and/or diglyceride of a $C_{12}$–$C_{18}$ fatty acid, or a paraffin wax.

13 Claims, No Drawings

HAIR CARE AND AFTERTREATMENT PREPARATIONS

BACKGROUND OF THE INVENTION

1. Field of the Invention

This invention relates to cosmetic hair care and aftertreatment preparations adapted for the improvement of the condition or appearance of the hair, containing as an emulsifying agent a quaternary ammonium compound containing two oxyalkylated fatty alkyl groups substituted on the quaternary nitrogen atom. The cosmetic preparations according to the invention are compositions which are applied to the hair after shampooing to improve, inter alia, combability, shine, and body, and to reduce static charge, and which are then rinsed from the hair; cosmetic preparations according to the invention also include compositions which are applied to the hair to improve structure or to promote or accomplish setting, water waving, permanent waving, coloring or bleaching.

2. Discussion of Related Art

Quaternary ammonium compounds have long been used in cosmetic haircare preparations because of their substantivity and their antistatic and revitalizing properties. However, quaternary ammonium compounds substituted with a single long-chain fatty alkyl group at the quaternary nitrogen atom typically exhibit good antistatic properties but poor revitalizing effects, whereas those substituted with two long-chain fatty alkyl groups at the quaternary nitrogen atom usually have a better hair revitalizing effect, but limited emulsifying power. Accordingly, additional emulsifiers, fiers, usually nonionic, have to be used in emulsion-type compositions containing such disubstituted quaternary ammonium compounds.

BRIEF DESCRIPTION OF THE INVENTION

It has now been found that quaternary ammonium compounds substituted on the quaternary nitrogen atom with two alkoxylated fatty alkyl groups exhibit improved hair revitalization and also improved emulsification properties for oil and fatty components in the cosmetic preparations of the invention.

DETAILED DESCRIPTION OF THE INVENTION

Other than in the operating examples, or where otherwise indicated, all numbers expressing quantities of ingredients or reaction conditions used herein are to be understood as modified in all instances by the term "about".

The invention accordingly comprises cosmetic hair care and aftertreatment preparations containing surface-active quaternary ammonium compounds corresponding to the following formula (I):

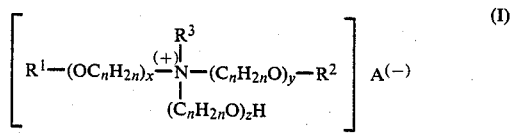

in which $R^1$ and $R^2$ are linear $C_8$–$C_{22}$ alkyl; RHu 3 is $C_1$–$C_4$ alkyl, benzyl, or —$(C_nH_{2n}O)_zH$; n=2 or 3; x, y, and z are each independently from 1 to 20; and A is the anion of a mineral acid, especially chloride, bromide, sulfate, or phosphate, the anion of a lower carboxylic acid, or is $R^4OSO_3^{(-)}$, wherein $R^4$ is $C_1$–$C_4$-alkyl.

Preparations according to the invention preferably contain quaternary ammonium compounds of formula I wherein $R^1$ and $R^2$ are linear $C_{16}$–$C_{18}$ alkyl and $R^3$ is methyl or hydroxyethyl.

The quaternary ammonium compounds corresponding to formula I are conveniently prepared from tertiary ether amines corresponding to the following formula (II):

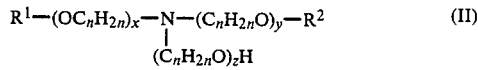

by quaternization with a suitable reactant, particularly a $C_1$–$C_4$-alkyl halide, a dialkyl sulfate containing a $C_1$–$C_4$-alkyl group, a benzyl halide, or propylene or ethylene oxide. Alternatively, the quaternary ammonium compounds of the formula I are conveniently prepared from tertiary ether amines corresponding to formula (III):

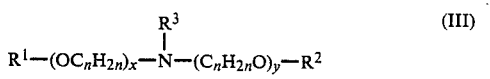

by quaternization with ethylene or propylene oxide. The quaternizations are carried out by methods known in the art. Quaternization of the ether amines of formula II with ethylene oxide gives a quaternary ammonium hydroxide corresponding to formula I, in which $R^3$ is —$(C_nH_{2n}O)_zH$, wherein n is 2. This then is converted into the corresponding salt by neutralization, for example with a mineral acid or a water-soluble carboxylic acid containing from 1 to 4 carbon atoms. In these cases, $A^{(-)}$ may also be the anion of a different mineral acid, for example a sulfate or phosphate anion, or the carboxyl residue of a lower carboxylic acid, such as a $C_1$–$C_6$-carboxylic acid, for example an acetate, glycolate, lactate, citrate or tartrate anion.

Tertiary ether amines corresponding to formula III are conveniently obtained from tertiary ether amines corresponding to the following formula (IV):

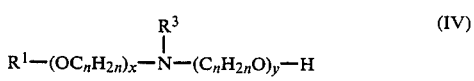

by alkylation at the hydroxyl group using sulfuric acid semiesters or sulfuric acid semiester salts of $C_8$–$C_{22}$ fatty alcohols, or mixtures thereof, as known in the art. A particularly elegant process for the production of such tertiary ether amines is described in U.S. patent application Ser. No. 827,844, filed Feb. 7, 1986; now U.S. Pat. No. 4,650,865 the production of two previously unknown quaternary ammonium compounds corresponding to formula I is exemplified therein. According to this process, compounds of the formula II are conveniently prepared from triethanol amine by alkylation at 2 hydroxyl groups by using sulfuric acid semiesters or semiester salts of $R^1$- and $R^2$-fatty alcohols. Quaternary ammonium compounds corresponding to formula I, in which y and optionally z have values of greater than 1, may be obtained from teritary ether amines corresponding to formula IV, wherein y is 1, by addition of (y−1) moles alkoxide, particularly ethylene oxide, in known manner, alkylation to the compound corresponding to formula III and quaternization with $z$ moles of a selected alkoxide as described above.

In formulae II, III and IV, $R^1$, $R^2$, $R^3$, n, x, y and z have the same meanings as defined for formula I.

One preferred embodiment of the invention comprises cosmetic preparations for the aftertreatment of hair after shampooing, referred to herein as hair rinses. The rinses according to this embodiment broadly comprises oil-in-water emulsions containing from 0.1 to 5% by weight of a quaternary ammonium compound of formula I and, in addition, a water-insoluble oil and/or fatty component, preferably a $C_{12}$–$C_{18}$ fatty alcohol, a monoglyceride and/or diglyceride of a $C_{12}$–$C_{18}$ fatty acid, or paraffin wax. Other suitable oil and/or fatty components include cosmetic oils, for example 2-octyl dodecanol; fatty acid ($C_8$–$C_{10}$) triglycerides; oleyl erucate; decyl oleate; isopropyl stearate; squalene; and fatty or wax components, such as lanolin, spermaceti, japan wax, beeswax or synthetic substitutes for these natural materials. The cosmetic oil or fatty components are preferably present in the cosmetic rinse preparations in a quantity of from 0.2 to 10% by weight. These hair rinse preparations optionally further include other standard cosmetic ingredients, for example nonionic surfactants; cationic surfactants such as quaternary ammonium compounds substituted with a single fatty alkyl group at the nitrogen atom; water-soluble cationic polymers; water-soluble nonionic polymers; nonionic emulsifiers; propylene glycol; glycerol; glucose; herb extracts; vitamins; sebostatics; anti-dandruff agents; preservatives; dyes; fragrances; opacifiers; and pearlizers, all in conventional quantities.

In another preferred embodiment, cosmetic hair care preparations comprising clear, aqueous or aqueous-alcoholic, liquid or gel-form compositions containing from 0.1 to 5% by weight of the quaternary ammonium compound of formula I in combination with a thickening, setting, or conditioning water-soluble polymer of the type known in the art in a quantity of from 0.1 to 5% by weight (percentages based on the weight of the composition), are provided. Suitable water-soluble polymers include anionic, cationic or non-ionic water-soluble polymers having an average molecular weight of from 1,000 to 1,000,000.

Useful anionic polymers include, for example, polymers of acrylic acid, methacrylic acid, crotonic acid, itaconic acid and maleic acid, and copolymers thereof with a monoethylenically unsaturated monomer, especially ethylene, vinyl benzene, vinyl acetate, vinyl methyl ether, or acrylamide. Other suitable anionic polymers include polymers containing carboxyl, carboxylate, or aldehyde groups such as the polymers described in German patent application No. 24 52 031 and commercially available as POC TM, or the crosslinked acrylic acid polymers described in U.S. Pat. No. 2 798 053 and commercially available as Carbopol TM. Water-soluble carboxymethyl celluloses or carboxymethyl starch are also useful. Suitable cationic polymers are, for example, the quaternized polymers and copolymers of dimethyl diallyl ammonium chloride described in U.S. Pat. No. 3,912,808 and commercially available as Merquat TM 100 or Merquat TM 500, the cationic cellulose ethers described in U.S. Pat. No. 3,472,840 and commerically available as Polymer JR TM 400, the cationic polyvinyl pyrrolidone copolymers described in U.S. Pat. No. 3,910,862 and commercially available as Gafquat TM 734 and 755, the copolymers of adipic acid and dimethylaminohydroxypropyl diethylene triamine described in U.S. Pat. No. 3,632,559 and commercially available as Cartaretin TM F4, and the quaternary polymeric urea derivatives described in U.S. Pat. No. 4,157,388 and commercially available as Mirapol TM A15.

Suitable nonionic polymers are, for example, polyvinyl pyrrolidone such as those commercially available as Luviskol TM products, Kollidon TM, or hydroxyethyl celluloses, hydroxy-propyl celluloses or methyl hydroxypropyl cellulose. These clear, liquid or gelform preparations may also contain other standard cosmetic ingredients, for example nonionic surfactants or emulsifiers, propylene glycol, glycerol, glucose, herb extracts, vitamins, sebostatics, anti-dandruff agents, preservatives, dyes and perfumes in the usual quantities.

The following Examples are illustrative of the invention and do not limit it in any way:

EXAMPLES

EXAMPLE 1

Preparation of di-(cetyl/stearyloxyethyl)-dimethylammonium chloride

A. Preparation of cetyl/stearyloxyethyl-hydroxyethyl-methylamine 334 g (1 mol) cetyl/stearyl (30:70) sulfuric acid half ester 143 g (1.2 mol) N-methyldiethanolamine, and 84 g (2.1 mol) sodium hydroxide were mixed under cooling and the mixture gradually heated to 160° C., wherein water was distilled off above 120° C. After a reaction time of 2 hours at 170° C., the mixture was cooled to 80° C., washed with saturated sodium chloride solution, then dried at 80° C. under vacuum on the rotary evaporator. Precipitated sodium chloride was filtered off. 292 g of a red brown liquid with an amine number of 96 and a hydroxyl number of 180 were obtained.

B. Preparation of di(cetyl/stearyloxyethyl)-methyl amine 240 g (0.411 mol) of the reaction product according to 1(A) were heated to 80° C. Then in portions 283.7 g (0.411 mol) cetyl/stearyl sulfate-sodium salt (56% paste) were added and the water distilled off under vacuum. Finally, 19.7 g sodium hydroxide were added and the batch heated to 200° C. After a reaction time of 3 hours the mixture was cooled to room temperature and washed twice with saturated sodium chloride solution at 80° C., and the reaction product then dried under vacuum in the rotary evaporator. The product had an amine number of 70.

C. Quaternization of di(cetyl/stearyloxyethyl)-methyl amine 208 g of the reaction product according to 1(B) were dissolved in 44.6 g isopropanol and 25.1 g $H_2O$ and reacted with 100 g methyl chloride in a pressure autoclave at 90° C. and 10 bar. After about 5 hours the reaction was complete. The amine number was 3. After expansion, water and isopropanol were removed in the reaction evaporator at 80° C. Di-(cetyl/stearyl/oxyethyl)-methyl amine ammonium chloride was recovered.

EXAMPLE 2

Preparation of cetyl/stearylpoly(6)oxyethyl-cetyl/stearyloxyethyl-hydroxyethyl-methyl-ammonium chloride A. Preparation of cetyl/stearylpoly(6)oxyethyl-dihydroxyethyl amine 1635 g cetyl/stearyl (30:70) poly(5)oxyethyl sulfuric acid semiester, 582.2 g triethanolamine and 566.4 g sodium hydroxide solution (50% by weight in water) were mixed while cooling and the resulting mixture heated to 175° C., water being distilled off under reduced pressure beyond 100° C. After a reaction time of 2 hours at 200° C., the reaction mixture was cooled to 80° C., washed with saturated sodium chloride solution and then dried in vacuo at 80° C. in a rotary evaporator. 1460 g of a dark oil having an amine number of 69.3 and a hydroxyl number of 140.6 were obtained.

B. Preparation of cetyl/stearylpoly(6)oxyethyl-cetyl/stearyloxyethylhydroxyethyl amine 300 g (0.375 mole) of the reaction product from (2)(A) was heated to 80° C. 258.8 g (0.375 mole) cetyl/stearyl sulfate, sodium salt (55% paste) were then added in portions and the water was distilled off in vacuo. Finally, 18.0 g (0.45 mole) sodium hydroxide were added and the mixture heated to 175° C. After a reaction time of 2 hours, the reaction mixture was cooled to 80° C. and washed twice with saturated sodium chloride solution. The reaction product was then dried in vacuo in a rotary evaporator.

C. Quaternization of cetyl/stearyl poly(6)oxyethyl-cetyl/stearyloxyethyl-hydroxyethyl amine 187.5 g of the reaction product from (2)(B) were dissolved in 40 g isopropanol and 22.5 g water and reacted with 100 g methyl chloride at 90° C./10 bar in a pressure autoclave. The reaction was over after about 4 hours. After venting, water and isopropanol were removed at 80° C. in a rotary evaporator. Cetyl/stearylpoly(6)oxyethyl-cetyl/stearyloxyethyl-hydroxyethyl-methyl-ammonium chloride was recovered.

EXAMPLE 3

Preparation of di-(cetyl/stearyloxyethyl)-hydroxyethylmethyl-ammonium chloride

A. Preparation of cetyl/stearyloxyethyl-dihydroxyethyl amine
 21.0 kg (30.4 moles) cetyl/stearyl sulfate, Na salt (55% paste)
 10.7 kg (72 moles) triethanolamine and
 1.74 g (43 moles) sodium hydroxide
were mixed by introducing the triethanolamine into the reactor and adding the cetyl/stearyl sulfate, Na salt, in portions, followed by the removal of water under reduced pressure. The sodium hydroxide was then added. After a reaction time of 2 hours at 175° C., the reaction mixture was cooled to 80° C., washed twice with deionized water and then dried in vacuo at 110° C. 12.5 kg of a yellowish solid product having an amine number of 135 were obtained.

B. Preparation of di-(cetyl/stearyloxyethyl)-hydroxyethyl amine 8 kg (19.8 moles) of the reaction product from (3)(A) was heated to 90° C. 13.4 kg (19.8 moles) cetyl/stearyl sulfate, Na salt (55% paste) was then added in portions and the water distilled off in vacuo. Finally, 930 g sodium hydroxide were added and the mixture heated to 200° C. After a reaction time of 3 hours, the reaction product was washed twice with deionized water at 95° C. and thereafter was dried in vacuo at 110° C. 12 g of a pale yellow solid product having an amine number of 84 were obtained.

C. Quaternization of di-(cetyl/stearyloxyethyl)-hydroxyethyl amine 500 g of the reaction product from (3)(B) was dissolved in 107 g isopropanol and 60 g water and the resulting solution reacted with 200 g methyl chloride in a pressure autoclave at 90° C./5 bar. The reaction was over after about 2.5 hours. After venting, water and isopropanol were removed in a rotary evaporator at 80° C. Di-(cetyl/stearyloxyethyl)-hydroxyethylmethyl ammonium chloride was recovered.

EXAMPLE 4

Preparation of di-(cetyl/stearyloxyethyl)-di-(poly(3)oxyethyl)-ammonium lactate 224.5 g (0.31 mole) of the reaction product from (3)(B), 31.0 g (0.31 mole) lactic acid (90%) and 76.9 g water were introduced into a pressure autoclave. After purging with nitrogen, 67.8 g (1.54 moles) ethylene oxide were introduced at a temperature of 80° C. and under a maximum pressure of 5 bar. Following an after-reaction time of about 4 hours at 85° C. and subsequent venting, 396 g of a mass solid at room temperature and having an acid number of 0.7 were obtained.

EXAMPLE 5

A hair rinse according to the invention was prepared by admixing the following ingredients:

| Ingredient | % by weight |
| --- | --- |
| Product of Example 2(C) | 1 |
| Cetyl/stearyl alcohol (50:50) | 1.5 |
| Water | ad 100 |

EXAMPLE 6

A blow-wave lotion according to the invention was prepared by admixing the following ingredients:

| Ingredient | % by weight |
| --- | --- |
| Ethanol | 30 |
| Gafquat TM 755 (1)* | 1 |
| Luviskol TM K 30 (2)* | 0.5 |
| Cremophor TM RH 30 (3)* | 0.3 |
| Product of Example (3) (C) | 0.15 |
| Water | ad 100 |

*see Appendix
APPENDIX
The following commercial products were used in the Examples:
(1) Gafquat TM 755: A copolymer of methacrylic acid dimethylaminoethyl ester and vinyl pyrrolidone quaternized with dimethyl sulfate as described in U.S. Pat. No. 3,910,862; a product of GAF corporation, New York, N.Y., (USA).
(2) Luviskol TM K 30: Polyvinyl pyrrolidone, K-value: approx. 30; a product of BASF-AG, Ludwigshafen, Germany.
(3) Cremophor TM RH 30: Hydrogenated castor oil + 60 moles ethylene oxide; a product of BASF-AG, Ludwigshafen, Germany.

The following commercial products are mentioned in the specification:

POC TM; a product of Degussa AG, Frankfurt, Germany.

Carbopol TM; a product of B. F. Goodrich Chem. Group, Cleveland, Ohio, (USA).

Merquat TM 100 and 500; products of Merck & Co. Inc. Chem. Div., Rahway, N.Y., (USA).

Polymer JR TM 400; a product of Union Carbide Corp., New York, N.Y., (USA).

Gafquat TM 734; a product of GAF corporation, New York, N.Y., (USA).

Cartaretin TM 74; a product of Sandoz AG, Basel, Swizzerland.

Mirapol TM A15; a product of Miranol Chem. Co., Dayton N.Y., (USA).

Kollidon TM; a product of BASF AG, Ludwigshafen, Germany.

We claim:

1. In a cosmetic composition for improving the condition or appearance of the hair, the improvement comprising a surface-active quaternary ammonium compound of the following formula (I):

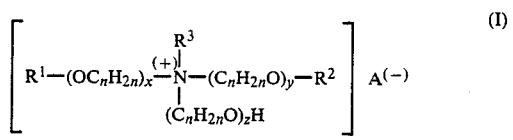

in which $R^1$ and $R^2$, independently of one another, are linear $C_8-C_{22}$ alkyl; $R^3$ is $C_1-C_4$-alkyl, benzyl, or $-(C_nH_{2n}O)_zH$; n is 2 or 3; x, y, and z are, independently of one another, 1 to 20; and A is the anion of a mineral acid, or of a $C_1-C_6$-carboxylic acid, or is $R^4OSO_3^{(-)}$, wherein $R^4$ is $C_1-C_4$ alkyl.

2. The cosmetic composition of claim 1, wherein $R^1$ and $R^2$ are $C_{16}-C_{18}$-alkyl and $R^3$ is methyl or hydroxyethyl.

3. The cosmetic composition of claim 1, wherein y and optionally z are greater than 1.

4. The cosmetic composition of claim 1, comprising an oil-in-water emulsion and further including a water-insoluble oil or fatty component, and wherein the quaternary ammonium compound is present in an amount of from about 0.1 to 5% by weight, based on the total weight of the composition.

5. The cosmetic composition of claim 4, wherein the fatty component is a $C_{12}-C_{18}$-fatty alcohol, a mono- or diglyceride of a $C_{12}-C_{18}$-fatty acid, or a paraffin wax.

6. The cosmetic composition of claim 4, wherein the oil or fatty component is 2-octyl dodecanol, a triglyceride of a $C_8-C_{10}$-fatty acid; oleyl erucate; decyl oleate; isopropyl stearate; squalene; or a natural fat or wax.

7. The cosmetic composition of claim 4, wherein the oil or fatty component is present in an amount of from about 0.2 to 10% by weight, based on the total weight of the composition.

8. The cosmetic composition of claim 1, comprising a clear aqueous or aqueous-alcoholic solution and further including a water-soluble polymer in an amount of from about 0.1 to 5% by weight, and wherein the quaternary ammonium compound is present in an amount of from about 0.1 to 5% by weight, each amount based on the total weight of the composition.

9. The cosmetic composition of claim 8, wherein the water soluble polymer is an anionic, cationic, or nonionic polymer having an average molecular weight of from about 1,000 to 1,000,000.

10. The cosmetic composition of claim 8, in the form of a gel.

11. The cosmetic composition of claim 8, in the form of a liquid.

12. The cosmetic composition of claim 4, formulated as a hair rinse.

13. The cosmetic composition of claim 8, formulated as a hair setting or conditioning composition, wherein the water-soluble polymer functions to promote setting, conditioning, or thickening of the hair.

* * * * *